United States Patent [19]

Canavesi et al.

[11] Patent Number: 5,070,062

[45] Date of Patent: Dec. 3, 1991

[54] OXYCHLORINATION CATALYST, THE METHOD FOR ITS PREPARATION

[75] Inventors: Roberto Canavesi; Ferdinando Ligorati, both of Milan, Italy

[73] Assignee: Enichem Synthesis S.p.A., Palermo, Italy

[21] Appl. No.: 474,212

[22] Filed: Feb. 1, 1990

Related U.S. Application Data

[63] Continuation of Ser. No. 152,138, Feb. 4, 1988, abandoned.

[30] Foreign Application Priority Data

Feb. 13, 1987 [IT] Italy .................. 19369 A/87

[51] Int. Cl.$^5$ .................................. B01J 27/122
[52] U.S. Cl. .......................... 502/225; 502/226
[58] Field of Search .................. 502/225, 226

[56] References Cited

U.S. PATENT DOCUMENTS

| | | | |
|---|---|---|---|
| 3,308,184 | 3/1967 | Bajars | 260/680 |
| 3,468,968 | 9/1969 | Baker | 502/225 X |
| 3,816,554 | 6/1974 | Rene et al. | 260/659 A |
| 4,124,534 | 11/1978 | Leitert et al. | 252/441 |
| 4,206,180 | 6/1980 | Campbell et al. | 422/190 |
| 4,323,716 | 4/1982 | Canavesi et al. | 570/243 |
| 4,339,620 | 7/1982 | Cowfer et al. | 570/243 |
| 4,377,491 | 3/1983 | Canavesi et al. | 502/225 X |
| 4,446,249 | 5/1984 | Eden | 502/225 |
| 4,451,683 | 5/1984 | Davies et al. | 570/224 |

FOREIGN PATENT DOCUMENTS 701913 1/1965 Canada .
1140657 1/1969 United Kingdom .

*Primary Examiner*—Olik Chaudhuri
*Assistant Examiner*—G. Fourson
*Attorney, Agent, or Firm*—Hedman, Gibson, Costigan & Hoare

[57] ABSTRACT

An oxychlorination catalyst is described which is constituted by porous particles of microspheroidal, or at least microcrystalline, alumina impregnated with cupric chloride and with the chloride of an alkali or alkaline-earth metal, in which the copper and the alklai or alkaline-earth metal are uniformly distributed over the entire surface area of the particles. The method for the preparation of the catalyst is also described. The catalyst enables oxychlorination of ethylene to dichloroethane to be achieved with improved fluodynamic behavior of the fluidized catalytic bed and with improved conversions and selectivity towards the useful reaction product.

6 Claims, No Drawings

OXYCHLORINATION CATALYST, THE METHOD FOR ITS PREPARATION

This is a continuation of application Ser. No. 152,138, filed 2/4/88, now abandoned.

The present invention relates to an oxychlorination catalyst, the method for its preparation and its use in the oxychlorination of ethylene to dichloroethane.

The oxychlorination of ethylene to dichloroethane by means of hydrogen chloride and air, or oxygen, is a method which is well known in the art. In order to accelerate this reaction, catalysts constituted by halides (particularly chlorides) of variable-valence metals, particularly cupric chloride, are used. This latter salt, which may be used alone, or in combination with other promoters, is supported on mineral substances, particularly alumina.

The oxychlorination of ethylene is generally carried out by the passage of a gaseous mixture containing ethylene, hydrogen chloride and oxygen, or air, through a reaction chamber containing the catalyst in the form of fluidised solid particles.

The disadvantages of the known catalysts lie, generally, in the volatility of the copper salt, in the low activity and selectivity towards the useful reaction product and in the poor quality of fluidisation under the oxychlorination conditions.

In published European patent application No. 58644, a catalyst is described which is constituted by porous particles of alumina impregnated with cupric chloride, in which the copper is uniformly distributed over the entire surface area of the particles, with a degree of irregularity no greater than ±7%.

This catalyst displays good fluidisation characteristics under the particular conditions of the reaction for the oxychlorination of ethylene and also enables dichloroethane to be produced with good reagent conversion and selectivity values.

It has now been found that it is possible to obtain a further improvement both in the fluodynamic performance of the fluidised catalyst, and in the conversion and selectivity values exhibited in the oxychlorination of ethylene, when the catalysts of the European patent application cited above also contain measured quantities of at least one alkali or alkaline-earth metal chloride, uniformly distributed over the entire surface area of the particles.

It should be noted that the known technique taught the addition of a halide, particularly a chloride of an alkali or an alkaline-earth metal, for the purpose of reducing the volatility of the cupric chloride in the oxychlorination catalyst.

The addition of the alkali or alkaline-earth metal chloride according to the present invention, however, gives rise to effects such as an improvement in the fluidisation characteristics and in the performance of the ethylene during oxychlorination, which could not be foreseen on the basis of this prior art.

Accordingly, the oxychlorination catalyst of the present invention is constituted by a support of porous, microspheroidal, or at least microcrystalline, alumina particles impregnated with cupric chloride and with at least one chloride of an alkali or alkaline-earth metal, and is characterised in that the cupric chloride content varies from 3 to 7% by weight (expressed in terms of the metal), the alkali or alkaline-earth metal chloride content varies from 0.01 to 4.0% by weight (expressed in terms of the metal) and the copper and the alkali or alkaline-earth metal are uniformly distributed over the entire surface area of the particles, with a degree of irregularity no greater than ±7%.

Alumina which is useful as the support for the catalysts of the present invention has the following characteristics:

porous particles with an average diameter of from 30 to 50 microns; no particles larger than 110–120 microns; no more than 5% of the particles less than 20 microns;
surface area: from 120 to 220 $m^2/g$;
pore volume: from 0.35 to 0.6 ml/g
average pore radius: from 40 to 70 Angstroms.

In the preferred embodiment, the alumina used as the support has characteristics within the following ranges of values:
surface area: from 140 to 200 $m^2/g$;
pore volume: from 0.40 to 0.55 ml/g.

Preferably the content of any silica in the alumina is less than 0.1%, any iron content does not exceed 0.03% and any $Na_2O$ content does not exceed 0.01% by weight.

The alkali or alkaline-earth metal chlorides for use in the catalysts of the present invention may generally be selected from those of lithium, sodium, potassium, rubidium, caesium, beryllium, magnesium, calcium, strontium and barium. Lithium, potassium, strontium, calcium, barium and magnesium chlorides are preferred.

A single alkali or alkaline-earth metal chloride may be used in the catalyst, or two or more of these chlorides may be used.

Furthermore, in the preferred embodiment, the catalysts contain quantities of cupric chloride of the order of 4–5% by weight (expressed in terms of the copper metal) and the alkali or alkaline-earth metal chloride in quantities of the order of 0.1–1.5% by weight (expressed in terms of the metal).

The method for the preparation of the catalyst according to the present invention comprises the following steps carried out in succession:
a) thermal treatment of the porous alumina particles by heating to 250–500 degrees Centigrade for a period of from 1 to 5 hours;
b) fluidisation of the heated particles by means of a flow of gas kept at a temperature no higher than 50 degrees Centigrade;
c) impregnation of the particles in the fluidised bed with the use of a volume of an aqueous solution of cupric chloride and alkali or alkaline-earth metal chloride of from 0.7 to 0.9 times the total pore volume of the particles;
d) heating of the fluidisation gas at a gradient of from 5 to 30 Centigrade degrees/hour to a temperature of approximately 140 degrees Centigrade and maintaining this temperature for from 0.5 to 15 hours;
e) activation in the fluidised state with oxygen, or oxygen-containing gas, at a temperature of from 150 to 250 degrees Centigrade, for a period of from 4 to 24 hours.

In the preferred embodiment of the method of the present invention:
in step (a) the heat treatment is carried out for 2–3.5 hours at 300–430 degrees Centigrade;
in step (b) air is used as the fluidisation gas;
in step (c) the impregnation is carried out with an aqueous solution containing from 20 to 40 g of $CuCl_2$ and from 1 to 20 g of at least one alkali or alkaline-earth metal chloride for each 100 ml of the impregnation solution;

the time for heating to approximately 140 degrees Centigrade in step (d) varies from 1 to 10 hours;

the activation step (e) takes place in the same reactor as that used for the oxychlorination of ethylene.

The catalyst of the present invention is used in the form of a fluidised bed for the oxychlorination of ethylene to dichloroethane. This method is carried out by the supply of a flow of ethylene, oxygen and hydrogen chloride in a molar ratio of from 1.01:0.6:2 to 1.06:0.85:2, with the rate of flow in the reactor adjusted to a value of from 9 to 40 cm/sec, and at a temperature of from 215 to 260 degrees Centigrade and at a pressure of from 2 to 6 Kg/cm$^2$.

Furthermore, air or pure, or substantially-pure, oxygen may be used as the oxygen-bearing gas and the exhausted gases may, but need not, be recycled.

In each case the fluodynamic behaviour of the fluidised bed is excellent and, at any rate, better than that of a similar catalyst without an alkali or alkaline-earth metal chloride, particularly in the following aspects: absence of bubbles in the fluidised bed, absence of "sticking" and entrainment of the catalyst into the cyclone separators.

Furthermore, it is possible, by means of the catalyst of the present invention, to improve the conversion of ethylene to dichloroethane whatever the ratio of the reagents supplied, that is compared with similar catalysts without an alkali or alkaline-earth metal chloride, as will become clear from the experimental examples given below.

The support for the catalyst according to published European patent application 58644 must conform to a set of critical values, particularly as regards its weight loss on heating, its surface area and its pore volume.

It has been found, unexpectedly, that when, according to the present invention, an alkali or an alkaline-earth metal chloride is added to the catalyst, the value of the weight loss on heating has almost no effect and the values of the surface area and the pore volume of the alumina used as the support are less critical. This is advantageous in that the alumina may be selected from a wider range of commercially-available products.

The following experimental examples are illustrative of, and not limiting with regard to, the scope of the invention.

EXAMPLE 1

Commercial alumina was used, having the following characteristics:

average particle size: 40 microns; no particles larger than 100 microns; 4–5% of particles smaller than 20 microns (determination by means of a sedimentation balance);

surface area: 150 m$^2$/g (B.E.T. determination after degassing for three hours at 200 degrees Centigrade);

pore volume: 0.48 ml/g (B.E.T. determination);

average pore radius: 64 Angstrom (B.E.T. determination).

The alumina also had a silica content of less than 0.1% by weight, an iron content of less than 0.03% by weight and a Na$_2$O content of less than 0.01% by weight.

The alumina was treated in an oven at 380 degrees Centigrade for three hours.

The alumina, thus treated (890 g) was placed in a cylindrical reactor with an internal diameter of 60 mm provided with a porous wall at the base. Air was delivered through this wall at a flow rate of approximately 500 l/hour so as to ensure a linear velocity of the gas of approximately 5cm/sec to obtain good fluidisation of the alumina particles.

340 ml of an aqueous solution containing 107 g of cupric chloride (CuCl$_2$.2H$_2$O) and 37 g of calcium chloride (CaCl$_2$.2H$_2$O) were prepared separately.

In this way, the volume of the impregnating solution was approximately 80% of the total pore volume of the alumina.

This solution was added dropwise to the top of the cylindrical receptacle, in the centre of the fluidised bed. The solution was supplied over a period of 60 minutes and the whole operation was carried out at ambient temperature (20–25 degrees Centigrade).

On completion of the impregnation, the fluidisation air was heated at an hourly gradient of 30 Centigrade degrees until a maximum temperature of 140 degrees Centigrade was reached. The air was maintained at this temperature for the next 2 hours and then cooled and the particles were loaded into a tubular glass reactor with an internal diameter of 40mm, provided with a thermocouple at its centre, where activation was carried out under fluidised conditions with air at 180 degrees Centigrade for 15 hours.

The catalyst thus obtained (catalyst A) contained 4% by weight of copper (assessed as the metal) and 1% by weight of calcium chloride (assessed as the metal). The copper and the calcium were distributed over the entire surface area with a degree of irregularity of ±7% by weight, as determined by means of a JEOL electronic probe (model 50/A) and by the method described in published European patent application No. 58644.

EXAMPLE 2

A catalyst (catalyst B) was prepared in the same way as in example 1 with the use of an alumina support having the following characteristics:

surface area: 170 m$^2$/g;

pore volume: 0.54 ml/g;

average pore radius: 63 Angstroms.

A catalyst was obtained containing 4.5% by weight of copper (assessed as the metal) 1.2% by weight of calcium chloride (assessed as the metal) and 0.2% by weight of magnesium chloride (assessed as the metal) in which the copper, the calcium and the magnesium were distributed over the entire surface area with a degree of irregularity of ±7%.

EXAMPLE 3

A catalyst (catalyst C) was prepared in the same way as in Example 1 with the use of an alumina support having the following characteristics:

surface area 200 m$^2$/g;

pore volume: 0.57 ml/g;

average pore radius: 57 Angstroms.

A catalyst was obtained containing 5% by weight of copper (assessed as the metal), 1.5% by weight of calcium chloride (assessed as the metal) and 0.2% of lithium chloride (assessed as the metal). The degree of irregularity in the distribution of the metals was ±7%.

EXAMPLE 4

The catalysts A, B and C obtained in Examples 1 to 3 above were evaluated under oxychlorination conditions in a pilot reactor. More particularly, the catalysts were loaded into a glass reactor having an internal diameter of 40 mm, provided with a thermocouple in the centre and supplied through the porous wall at its base with a gas flow containing:
hydrogen chloride: 278 l/hour;
ethylene: from 144.8 to 141.9 l/hour;
air: 556 l/hour,
the volumes being measured at 20 degrees Centigrade and 1Kg/cm².

The temperature in the reactor was 220 degrees Centigrade, the pressure was 4 atmospheres absolute and the contact time was 28-30 seconds.

The results are given in Tables 1 and 2 below.

In particular, Table 1 gives the ethylene conversion values and Table 2 shows the corresponding hydrogen chloride conversion values for the three catalysts A, B and C for the various hydrogen chloride/ethylene molar ratios supplied (expressed as the ratio of the chlorine atoms to carbon atoms in the two reagents).

In all these tests, a particularly-high proportion of the ethylene converted was transformed into dichloroethane.

TABLE 1

| Cl/C Ratio | (ethylene conversion) | | |
|---|---|---|---|
| | Catalyst A | Catalyst B | Catalyst C |
| 0.960 | 95.6 | 95.4 | 95.5 |
| 0.975 | 96.5 | 96.4 | 96.5 |
| 0.985 | 97.0 | 96.8 | 96.9 |

TABLE 2

| Cl/C Ratio | (hydrogen chloride conversion) | | |
|---|---|---|---|
| | Catalyst A | Catalyst B | Catalyst C |
| 0.960 | 99.9 | 99.6 | 99.6 |
| 0.975 | 99.4 | 99.25 | 99.3 |
| 0.985 | 99.1 | 98.8 | 98.9 |

In all the tests the fluidised bed behaved extremely well, this assessment taking into account gas bubbles in the bed, the frequency thereof, and in the extreme case, the formation of pistons. In practice none of these phenomena occurred in the catalytic bed during the course of the tests.

EXAMPLES 5-7

(comparison)

Three catalysts were prepared (catalysts D, E and F) from the alumina of Examples 1, 2 and 3 respectively. In particular, the preparations were carried out in the same way as in Example 1, the catalyst D being prepared with 4% by weight of copper, the catalyst E with 5% by weight of copper and the catalyst F with 5% by weight of copper (still assessed as the metal). No alkali or alkaline-earth metal chloride was added to the these catalysts.

In the catalysts thus obtained, the copper was also distributed over the entire surface area with a degree of irregularity of ±7%.

These catalysts were used for the oxychlorination of ethylene under the conditions described in Example 4. The results obtained are given in Tables 3 and 4.

More particularly, Table 3 gives the ethylene conversions and Table 4 gives the hydrogen chloride conversions for the various ethylene/oxygen molar ratios used in the tests. In all these tests the ethylene converted was transformed practically completely into dichloroethane.

TABLE 3

| Cl/C Ratio | (ethylene conversion) | | |
|---|---|---|---|
| | Catalyst D | Catalyst E | Catalyst F |
| 0.960 | 94.9 | 94.9 | 94.7 |
| 0.975 | 95.8 | 95.9 | 95.7 |
| 0.985 | 96.3 | 96.2 | 96.1 |

TABLE 4

| Cl/C Ratio | (hydrogen chloride conversion) | | |
|---|---|---|---|
| | Catalyst D | Catalyst E | Catalyst F |
| 0.960 | 99.3 | 99.2 | 99.1 |
| 0.975 | 98.8 | 98.8 | 98.6 |
| 0.985 | 98.3 | 98.2 | 97.9 |

Taking into account the factors assessed in the preceding example, the catalyst F behaved well on fluidisation, the catalyst E behaved moderately and no formation of the piston was found with the catalyst D.

EXAMPLE 8

This was carried out in the same way as Example 1, with the alumina used in Example 1, and a catalyst (catalyst G) was prepared containing 4% by weight of copper (assessed as the metal), 1% by weight of calcium chloride and 0.1% by weight of lithium chloride (assessed as the metals).

The catalyst thus obtained, which contained copper, calcium and lithium distributed over the entire surface area with a degree of irregularity of ±7%, was used for oxychlorination of ethylene in the pilot reactor of Example 4, under the following reaction conditions: pressure 5 atmospheres absolute, temperature 240 degrees Centigrade, contact time approximately 16 seconds, oxygen/ethylene molar ratio approximately 0.7/1 and hydrogen chloride/ethylene molar ratio 0.960/1; 0.975/1; and 0.985/1, (expressed as the chlorine/carbon ratio of the two reagents).

The results are given in Table 5 below.

For comparison, a further catalyst (catalyst H) was prepared from the alumina of Example 1, containing 5% by weight of copper (as the metal), uniformly distributed over the entire surface area. This catalyst was used in the oxychlorination of ethylene, carried out as indicated above with reference to catalyst G. The results of these tests are given in Table 6 below.

TABLE 5

| Cl/C Ratio | Conversion of ethylene into dichloroethane | Conversion of hydrogen chloride |
|---|---|---|
| 0.960 | 95.1 | 99.8 |
| 0.975 | 96.1 | 99.3 |
| 0.985 | 96.7 | 98.9 |

TABLE 6

| Cl/C Ratio | Conversion of ethylene into dichloroethane | Conversion of hydrogen chloride |
|---|---|---|
| 0.960 | 94.5 | 99.3 |
| 0.975 | 95.4 | 98.6 |
| 0.985 | 95.9 | 98.1 |

In the case of the catalyst G the fluidised bed behaved very well. In the case of the catalyst H, the fluidised bed was found to be unstable and bubbles formed.

What is claimed is:

1. An oxychlorination catalyst which consists essentially of microspheroidal alumina particles impregnated with cupric chloride and with at least one metal chloride which is either calcium chloride alone or the combination of calcium chloride and lithium chloride content is from 3 to 7% by weight, expressed in terms of the copper metal, and the metal chloride content is from 0.01 to 4.0% by weight, expressed in terms of the alkali and alkaline-earth metal, and wherein the copper and the at least one metal chloride is distributed uniformly over the entire surface of said alumina particles with a degree of non-uniformity of not more than ±7%.

2. The catalyst as in claim 1, wherein the porous microspheroidal alumina particles have average diameter of from 30 to 50 microns, surface area of from 120 to 220 $m^2/g$, pore volume of from 0.35 to 0.6 ml/g, and average pore radius of from 40 to 70 Angstroms.

3. The catalyst as in claim 2, wherein the alumina particles have surface area of from 140 to 200 $m^2/g$ and pore volume of from 0.40 to 0.55 ml/g.

4. The catalyst as in claim 1, wherein the cupric chloride content is about 4-5% by weight, expressed in terms of the copper metal, and the metal chloride content is about 0.1-1.5% by weight, expressed in terms of the alkali and alkaline-earth metal.

5. A process for preparing an oxychlorination catalyst consisting essentially of the following steps, carried out in succession:
  a) heating porous microspheroidal alumina particles to 250°-500° C. for 1-5 hours;
  b) fluidizing the heated particles to form a fluid bed by a flow of fluidizing gas kept at a temperature no higher than 50° C.;
  c) impregnating the particles in the fluid bed with a volume of from 0.7 to 0.8 times the total pore volume of the particles, of an aqueous solution of cupric chloride and at least one metal chloride which is either calcium chloride alone or the combination of calcium chloride and lithium chloride;
  d) heating the fluidizing gas with a temperature gradient of from 5° to 30° C./hour up to a temperature of approximately 140° C. and maintaining this temperature for a period of from 0.5 to 15 hours; and
  e) activating the impregnated particles in said fluid bed with oxygen, or a gas containing oxygen, at a temperature of from 150° to 250° C., for a period of from 4 to 24 hours.

6. The process as in claim 5, wherein step (a) heating is carried out at 300°-430° C. for 2-3.5 hours, step (b) fluidizing is carried out with air as the fluidizing gas, step (c) impregnating is carried out with the aqueous solution containing from 20 to 40 g of the cupric chloride and from 1 to 20 g of the metal chloride per 100 ml of the aqueous solution, step (d) heating its.carried out at approximately 140° C. for 1-10 hours, and step (e) activating is carried out in a oxychlorination reactor.

* * * * *